(12) United States Patent
Bachmann et al.

(10) Patent No.: US 6,224,377 B1
(45) Date of Patent: May 1, 2001

(54) DENTAL POST MADE OF RADIOPAQUE COMPOSITE

(76) Inventors: Marc William Bachmann; Sonia Bachmann; Noemie Bachmann, all of 20, rue Biron, 34190 Ganges (FR)

(*) Notice: Subject to any disclaimer, the term of this patent is extended or adjusted under 35 U.S.C. 154(b) by 0 days.

(21) Appl. No.: 09/323,612

(22) Filed: Jun. 1, 1999

(30) Foreign Application Priority Data

Sep. 29, 1998 (FR) .................................................. 98 12268

(51) Int. Cl.⁷ ...................................................... A61C 5/08
(52) U.S. Cl. ........................................ 433/220; 433/228.1
(58) Field of Search .................................... 433/220, 224, 433/226, 228.1

(56) References Cited

U.S. PATENT DOCUMENTS 4,474,942 * 10/1984 Sano et al. ........................... 528/363
5,741,139   4/1998 Sicurelli, Jr. et al. ................ 433/220
6,012,924 *  1/2000 Reynaud et al. ..................... 433/220

FOREIGN PATENT DOCUMENTS

| 2824214   | 12/1979 | (DE) . |
| 0432001A1 |  6/1991 | (EP) . |
| 2753365   |  3/1998 | (FR) . |
| WO96/26686 |  9/1996 | (WO) . |

* cited by examiner

*Primary Examiner*—John J. Wilson
(74) *Attorney, Agent, or Firm*—Ostrolenk, Faber, Gerb & Soffen, LLP

(57) ABSTRACT

Radiopaque dental post manufactured from a composite consisting of reinforcing fibers embedded in a resin matrix. The reinforcing fibers of the composite contain a zirconia radiopaque substance in an amount ranging from 10 to 30% by weight.

7 Claims, No Drawings

DENTAL POST MADE OF RADIOPAQUE COMPOSITE

The subject of the present invention is a dental post made of a radiopaque composite.

Composite corono-radicular dental posts intended for reconstructing the crowns of decayed teeth are increasingly tending to replace the metal-alloy posts used for decades.

This is because posts made of a precious or nonprecious alloy have several drawbacks:

they may be the seat of galvanic currents which create corrosion phenomena, with the liberation of metal ions;

their elastic modulus is ten times higher than that of define so that, during the masticatory function, by transferring the forces to which they are subjected to the dental member they may cause fractures in the root and the loss of the tooth in question.

Composite posts, consisting of a resin matrix in which reinforcing fibers are embedded, do not have these iatrogenic drawbacks.

Composite posts have been described in Patent FR-A-2, 626,167, FR-A-2,588,181 and EP-0,432,001.

These documents describe all the ways of manufacturing composite posts and the various reinforcing fibers and matrix resins that can be used.

The reinforcing fibers that can be used are carbon fibers, glass fibers, aramid fibers, Kevlar fibers or other such fibers.

The matrix resins that can be used are epoxy resins, polyvinyl esters or polymethacrylates.

However, all these fibers and resins are X-ray transparent, whereas it is very important for clinical dentists to be able to use X-rays to see the posts anchored in teeth.

The most obvious way of making the various composites used visible to X-rays could be to add a filler consisting of a radiopaque substance to the resin matrix; this has been tested, but the results obtained are far from being conclusive.

This is because the amount of resin generally employed for producing a high-quality composite is from 20 top 40% by volume, and the posts have a diameter of between 1 and 2 mm. Given the small amount of resin and the small diameter of the posts, it is difficult to add a radiopaque filler in sufficient quantity for the post to be visible in X-rays.

Moreover, introducing such a filler into the resin has the effect of increasing its viscosity: the resin thickens with, as a consequence, the reinforcing fibers being imperfectly wetted. The composite obtained has poor cohesion and its mechanical properties are substantially inferior.

In addition, the radiopaque filler is not distributed uniformly in the resin, but in a random fashion, which means that certain parts are rich in the radiopacifying substance while other parts contain none of it: the radiopacity obtained is not only low, but also irregular.

The object of the present invention is to remedy these drawbacks by proposing the use of a radiopaque reinforcing fiber for producing the composite used for manufacturing posts. The reinforcing fiber used may be a glass fiber, a quartz fiber or a silica fiber containing either barium glass or zirconium oxide, or zirconia, which are radiopaque substances.

The addition of zirconia or barium glass to the reinforcing fiber gives a radiopaque fiber which, used for the manufacture of the composite in an amount ranging from 60 to 80% by volume, gives the posts sufficient radiopacity, without adding any filler to the resin matrix.

The addition of zirconia or barium glass to the reinforcing fiber furthermore has the effect of making it alkali-resistant and of improving its mechanical properties, which mean a material particularly well suited to the production of dental posts can be made from the product.

The addition of zirconia or of barium glass to the reinforcing fiber is carried out during its manufacture, the chosen additive being introduced in powder form into the silica powder or the mixture of oxide powders serving for the manufacture of the glass.

The amount of zirconia or of barium glass in the reinforcing fiber is advantageously between 10 and 30% by weight, and preferably between 15 and 20% by weight.

The resin matrix of the composite may be an epoxy resin, a polyvinyl ester or a polymethacrylate.

The composite material may be obtained by various known processes, such as injection molding, pultrusion, compression-transfer molding, or a combination of these processes.

The dental posts manufactured using the radiopaque composite which has just been described are white or ivory in color and exhibit good radiopacity, without impairing their mechanical properties.

What is claimed is:

1. Radio-opaque dental post manufactured from a composite comprising reinforcing fibers embedded in a resin matrix, characterized in that the reinforcing fibers of said composite are glass containing between 15% and 30% by weight of zirconia.

2. Dental post according to claim 1, characterized in that the matrix of the composite consists of a resin chosen from epoxy resins, polyvinyl esters and polymethacrylates.

3. Dental post according to claim 2, characterized in that the composite contains from 20 to 40% by weight of resin and from 60 to 80% by volume of reinforcing fibers.

4. Dental post according to claim 1, characterized in that the reinforcing fibers contain from 15 to 20% by weight of zirconia.

5. Dental post according to claim 4, characterized in that the matrix of the composite consists of a resin chosen from epoxy resins, polyvinyl esters and polymethacrylates.

6. Dental post according to claim 5, characterized in that the composite contains from 20 to 40% by weight of resin and from 60 to 80% by volume of reinforcing fibers.

7. Dental post according to claim 1, characterized in that the composite contains from 20 to 40% by weight of resin and from 60 to 80% by volume of reinforcing fibers.

* * * * *

UNITED STATES PATENT AND TRADEMARK OFFICE
CERTIFICATE OF CORRECTION

PATENT NO.    : 6,224,377 B1
DATED         : May 1, 2001
INVENTOR(S)   : Marc W. Bachmann et al.

It is certified that error appears in the above-identified patent and that said Letters Patent is hereby corrected as shown below:

Column 1,
Line 13, change "define" to -- dentine --.

Column 2,
Line 33, should read:
 -- 1. Radio-opaque dental post manufactured from a composite comprising reinforcing fibers embedded in a resin matrix, characterized in that the reinforcing fibers of said composite are glass containing between 10% and 30% by weight of zirconia. --.

Signed and Sealed this

Seventh Day of March, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,224,377 B1 | Page 1 of 1 |
| APPLICATION NO. | : 09/323612 | |
| DATED | : May 1, 2001 | |
| INVENTOR(S) | : Marc W. Bachmann et al. | |

It is certified that error appears in the above-identified patent and that said Letters Patent is hereby corrected as shown below:

Col. 2, line 10:

Change "alkali-resistant" to --alkaline-resistant--.

Col. 2, line 41, Claim 3 should read:

3. Dental post according to claim 2, characterized in that the composite contains from 20 to 40% by ~~weight~~ volume of resin and from 60 to 80% by volume of reinforcing fibers.

Col. 2, line 50, Claim 6 should read:

6. Dental post according to claim 5, characterized in that the composite contains from 20 to 40% by ~~weight~~ volume of resin and from 60 to 80% by volume of reinforcing fibers.

Col. 2, line, 53, Claim 7 should read:

7. Dental post according to claim 1, characterized in that the composite contains from 20 to 40% by ~~weight~~ volume of resin and from 60 to 80% by volume of reinforcing fibers.

Signed and Sealed this

Tenth Day of October, 2006

JON W. DUDAS
*Director of the United States Patent and Trademark Office*